(12) United States Patent
Schoess

(10) Patent No.: US 6,718,819 B2
(45) Date of Patent: Apr. 13, 2004

(54) OIL QUALITY SENSOR SYSTEM, METHOD AND APPARATUS

(75) Inventor: Jeffrey N. Schoess, Buffalo, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 09/950,196

(22) Filed: Sep. 10, 2001

(65) Prior Publication Data

US 2003/0046985 A1 Mar. 13, 2003

(51) Int. Cl.[7] ............................................. G01N 33/26
(52) U.S. Cl. .................. 73/53.05; 324/448; 210/85; 210/86; 210/799; 210/416.5; 210/168; 210/167; 73/53.05; 73/61.61; 73/61.41
(58) Field of Search .................. 73/53.05, 61.41, 73/61.61; 324/448; 210/85, 86, 799, 416.5, 168, 167

(56) References Cited

U.S. PATENT DOCUMENTS

| | | | |
|---|---|---|---|
| 4,646,070 A | * | 2/1987 | Yasuhara et al. ............ 340/603 |
| 4,733,556 A | | 3/1988 | Meitzler et al. |
| 5,023,133 A | * | 6/1991 | Yodice et al. ............... 428/332 |
| 5,274,335 A | | 12/1993 | Wang et al. |
| 5,523,692 A | * | 6/1996 | Kuroyanagi et al. ........ 324/438 |
| 5,789,665 A | | 8/1998 | Voelker et al. |
| 5,929,754 A | | 7/1999 | Park et al. |

* cited by examiner

Primary Examiner—Hezron Williams
Assistant Examiner—André K. Jackson

(57) ABSTRACT

An apparatus for determining the condition of engine lubricating oil includes a sensor having a plurality of spaced apart electrode pairs on a nonconductive polymer film. The sensor is operatively associated with an oil filter, which provides retro-fit capability and easy access for servicing and replacement. The multi-electrode pair design averages signal output to reduce operational electromagnetic interference noise. A forcing-function waveform reactive circuit is applied to the sensor input electrode as a common voltage potential. The output current from the sensor electrodes is then relayed to a current follower amplifier, which converts the output current into an equivalent voltage for comparison with predetermined values. Based on the voltage values, the on-board sensing system will determine the oil's condition, and will trigger a trouble code if the equivalent voltage falls within a predetermined range.

6 Claims, 5 Drawing Sheets

OIL QUALITY SENSOR SYSTEM, METHOD AND APPARATUS

BACKGROUND OF THE INVENTION

1. Field of the Invention

The present invention relates to a system, method and apparatus for monitoring the condition of engine lubricating oil, and for detecting contamination and deterioration thereof. More particularly, the present invention relates to an oil monitoring system, method and apparatus including a sensor with multiple electrode pairs, mounted on a flexible non-conductive substrate, for receiving and reflecting a wave signal to monitor the quality and condition of engine oil.

2. Description of the Background Art

Detecting oil contamination and deterioration, in an internal combustion engine, is important in promoting and prolonging the useful life of the engine.

The usable life of motor oil depends on many factors, including the type of oil used, the engine's condition, ambient operating conditions, vehicle usage, and vehicle servicing. While most car manufacturers recommend changing the engine oil of an automobile at three months or three thousand miles, whichever comes first, many automobile owners and operators fail to regularly change the engine oil of their automobile within the recommended time frame.

Where deteriorated oil is subject to prolonged use because of infrequent oil changes, the useful life of an automobile engine is greatly reduced. The useful life of an automobile engine may also be reduced by the introduction of contaminants in the engine oil such as: water, antifreeze, or improper types of oil (e.g. four-stroke oil in a two-stroke engine). Accordingly, some types of oil monitoring methods and equipment, for detecting deterioration and contamination of engine lubricating oil, have been created.

Some examples of sensors for monitoring the condition of engine lubricating oil are illustrated in U.S. Pat. Nos. 4,733,556; 5,274,335; 5,789,665; and 5,929,754.

U.S. Pat. No. 4,733,556 issued to Meitzler et al. discloses an on-board sensor system which compares the dielectric properties of oil within an engine to the dielectric properties of unused oil contained in a sealed area, where both samples experience the same thermal cycling. As the engine oil is circulated through the engine, the on-board sensor continually compares the viscosity of the engine oil to the viscosity of a reference sample of oil, sealed in a container mounted between the engine block and the oil filter. When the viscosity of the two oils differ to a degree greater than a predetermined amount, the on-board sensor system signals that the engine's lubricating oil need be changed. The sealed oil is similar to the cycled oil, and hence is subject to the same thermal changes in viscosity. In the system of Meitzler et al., the detection of deteriorated oil may be skewed or delayed since the cycled oil is compared to potentially deteriorated oil in the sealed container. Additionally, this approach of monitoring oil quality does not quantify the actual effects of the oil, especially when oil is overstressed by abnormal engine operating conditions.

U.S. Pat. No. 5,274,335 issued to Wang et al. discloses an oil sensor system for detecting engine oil deterioration and contamination. This system involves a method of analyzing engine oil, and detecting oil viscosity and/or contamination, through the use of a dielectric monitoring apparatus, which measures the waveform between two closely placed electrodes (positioned 0.006 to 0.002 inches apart). The electrodes receive and retransmit a wave signal, which transfers information to an on-board monitoring station. When the system receives a signal having a value outside of a predetermined range, the internal sensor relays a message to an in-dash display, indicating the need for an oil change. This sensor system operates through dedicated hardwire implementation, in which the sensor probe is mounted in the engine's crankcase, and is in direct contact with the oil therein, to read the condition of the oil. As a practical matter, the installation of this type of dedicated hardwire implementation is only feasible during original engine assembly. In addition, since the design of Wang et al. uses only a single pair of electrodes, if there is any problem with this single pair of electrodes, the sensor will be rendered inoperable.

Since this sensor is located inside the engine crankcase, in the event of a sensor failure in the field, sensor replacement is a complex and difficult job, and probably can only be done by a dealer or specialist. The internal location of the sensor increases the difficulty and the cost of maintaining or repairing the sensor.

U.S. Pat. No. 5,789,665 issued to Voelker et al. discloses an engine oil deterioration sensor, which incorporates polystyrene resin beads impregnated with charged ions. The Voelker et al. invention includes an oil sensor attached to the oil pan, as a component of the oil drain plug, thereby utilizing another in-situ method of detection. The sensor housing contains three chambers, and a wire mesh divider is located between each chamber. As the oil deteriorates, the resin beads begin to shrink, and fall through the first wire mesh into the middle chamber. As the oil deteriorates further, the resin beads shrink further, and eventually fall through the second wire mesh lining into the third chamber, which triggers the warning sensor.

U.S. Pat. No. 5,929,754 issued to Park et al. describes a method for determining the minimum lubricating oil thickness within an operating engine, by measuring electrical capacitance of the engine oil. This measurement is calculated by determining the dispersion of an electrical signal as it travels from one electrode through the engine oil to another electrode. The electrode sensing section of the Park et al. invention is partially contained within a cylinder positioned inside the engine, providing in-situ detection. As the oil circulates through the engine, a portion of the oil also cycles through the cylinder via small ports within the cylinder wall. The Park et al. invention is located in on the engine similar to the Wang et al. device, in that it is bored into the engine block, which makes the Part et al. device available only on new cars during production and requires specialized repair and maintenance when the device wears.

While the known devices have shown some utility for their intended purposes, a need still exists in the fluid monitoring art for an apparatus that measures engine lubricating oil quality, through an in-situ system, without requiring specialized repair and maintenance. An oil-quality sensor is needed that can be serviced or changed by non-expert service personnel or by a vehicle owner or, if desired, when the device wears. In particular, there is a need for an oil-quality sensing device combining in-situ monitoring and detection with retro-fit capability, so that the system may be installed on vehicles currently in service.

SUMMARY OF THE INVENTION

The present invention has been developed to overcome limitations and disadvantages of known engine oil quality sensors, and to provide a cost-effective, reliable oil quality sensor.

The present invention provides a system, method and apparatus for sensing the condition of oil flowing through an operating oil filter. A sensor apparatus according to the invention may be incorporated into an oil filter assembly.

In accordance with a preferred embodiment, a system according to the present invention provides a multi-electrode sensor on a shape-conforming polymer thick film (PTF), a force-functioning waveform, a potentiostat circuit, and a waveform comparator.

Accordingly, it is an object of the present invention to provide a method and apparatus for detecting oil contamination and deterioration through in-situ monitoring and analysis.

In-situ monitoring offers a superior method of detection, as it monitors the actual oil circulated through the engine. However, proper location of the in-situ device is important for accurate monitoring, i.e. the sensor should be located in a spot where oil is actively circulated, rather than in a 'dead spot' (a location with little or no flow). The highest cycling area of engine oil is within or near the oil filter, and accordingly, the present invention incorporates in-situ detection using a sensor which is made part of the oil filter.

Such an in-situ oil monitoring device is advantageous because incorporation of the sensor into an otherwise conventional oil filter permits the inventive system to be retrofitted to any car, rather than limiting application to new cars only. This capability permits vehicle owners of all makes and models to reap the benefits of oil quality monitoring, which preserves life of their vehicles' engines. Incorporating the sensor into the oil filter also affords a cost-effective method of oil monitoring, as it requires no specifically designated mounting area and no separate maintenance; a worn sensor is removed and replaced as part of a new oil filter, during an oil change.

Another object of the present invention is to provide a flexible polymer thick film (PTF) as a component of the sensor. A printed sensor pattern on a polymer film permits sensor to conform to the shape of the surface into which it would be integrated, which provides for installation in tight locations or between two fitting surfaces where conventional sensors cannot fit. As a result, the sensor is capable of fitting on an tapping plate of an otherwise conventional oil filter.

Still another object of the present invention is to provide a sensor having multiple electrode pairs. Equipping the sensor with multiple electrode pairs provides advantages of improved sensor performance over single or double electrode design. Multi-electrode processing is advantageous because each electrode pair acts as an independent sensor element, sending multiple independent signals to the monitoring device which then relays an "averaged" sensor signal output. The signal-averaging approach potentially reduces operational electromagnetic interference (EMI) noise, which improves the signal-to-noise ratio of the sensor system. The multi-electrode design will also provide some redundancy support that increases system reliability.

Yet another feature of the present invention, due to its multi-sensor capability, is its ability to detect other types of fluids such as contaminated water, de-ionized water, antifreeze, and chlorinated solutions. For example, if an antifreeze leak condition occurs in an engine, the conductivity characteristics or antifreeze would serve as a unique marker with conductivity signature properties different from those exhibited by pure oil. The sensor array is able to detect this condition and provide warning information to a vehicle operator.

For a more complete understanding of the present invention, the reader is referred to the following detailed description section, which should be read in conjunction with the accompanying drawings. Throughout the following detailed description and in the drawings, like numbers refer to like parts.

DETAILED DESCRIPTION OF THE PREFERRED EMBODIMENT

1. Overview

Figure 1:
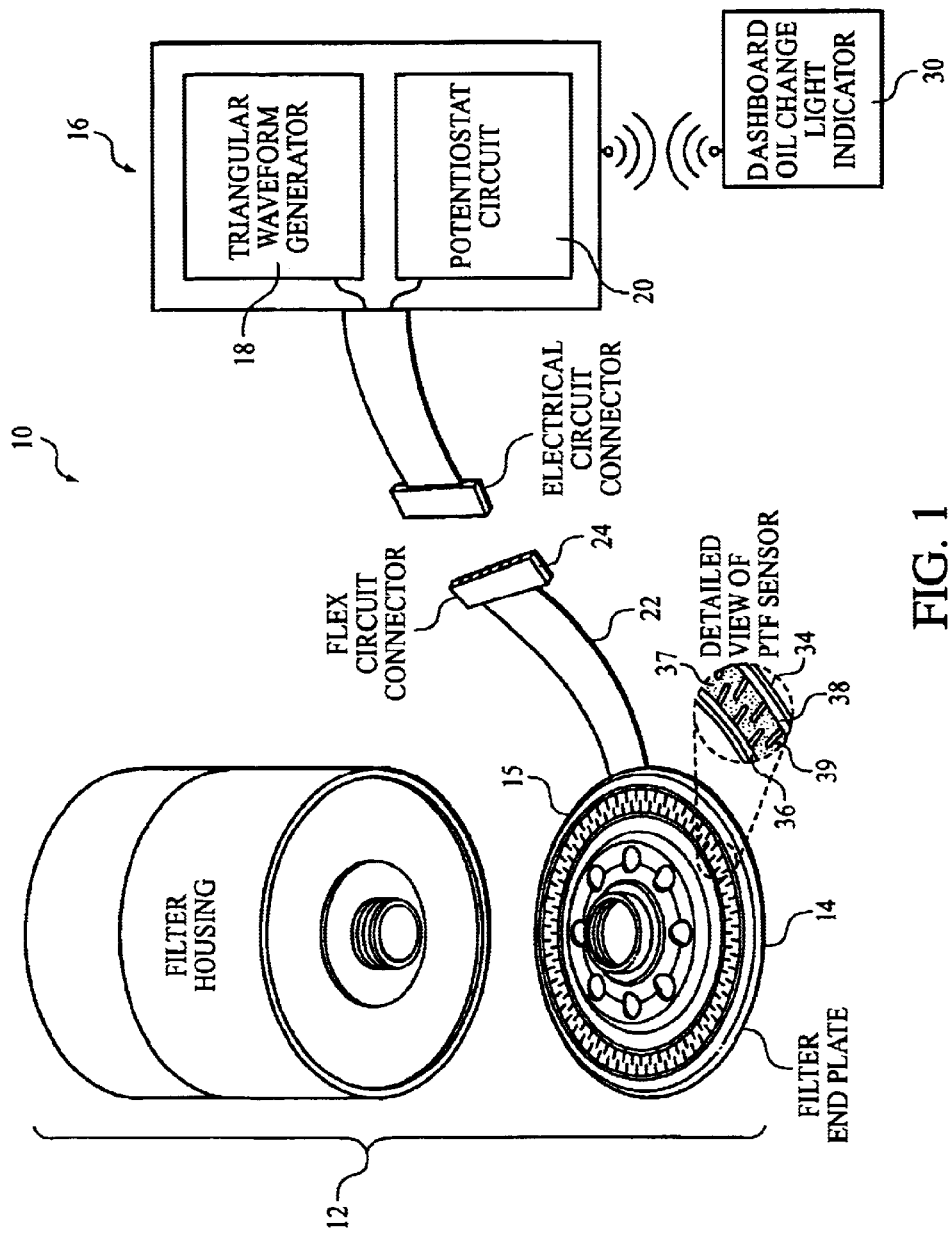
FIG. 1 is a simplified schematic diagram of an oil quality sensing system in accordance with a first embodiment of the invention.

Referring now to FIG. 1, an oil quality sensing system, in accordance with the present invention, is shown schematically at 10. The system 10 of the present invention includes an oil filter 12, which includes all of the components of a conventional spin-on type oil filter.

In addition to the conventional components, such as a housing, porous filter element, pressure relief valve, etc., the filter 12 also includes an oil quality sensor 15. In the embodiment of FIG. 1, the sensor 15 is provided as a substantially flat circular band placed on an inner surface of the filter tapping plate 14, for immersion in oil when the filter 12 is in operation.

The system 10 further includes a control module 16, for placement in electrical communication with the sensor 15. The control module 16 includes a waveform generator 18 and a potentiostat circuit 20. The control module 16 may further include a measuring device for measuring a signal reflected by the sensor 15, and a comparing device for comparing the measured signal to a set of reference values.

The control module 16 is connected to the sensor 15 by a ribbon cable 22 having a disconnectable plug assembly 24 thereon, to allow the oil filter 12 to be disconnectably separated from the control module 16. The control module 16 is also in electrical communication with a signal light 30 located on the dashboard of a vehicle (not shown).

Each of these system components will be described in further detail below.

Figure 2:
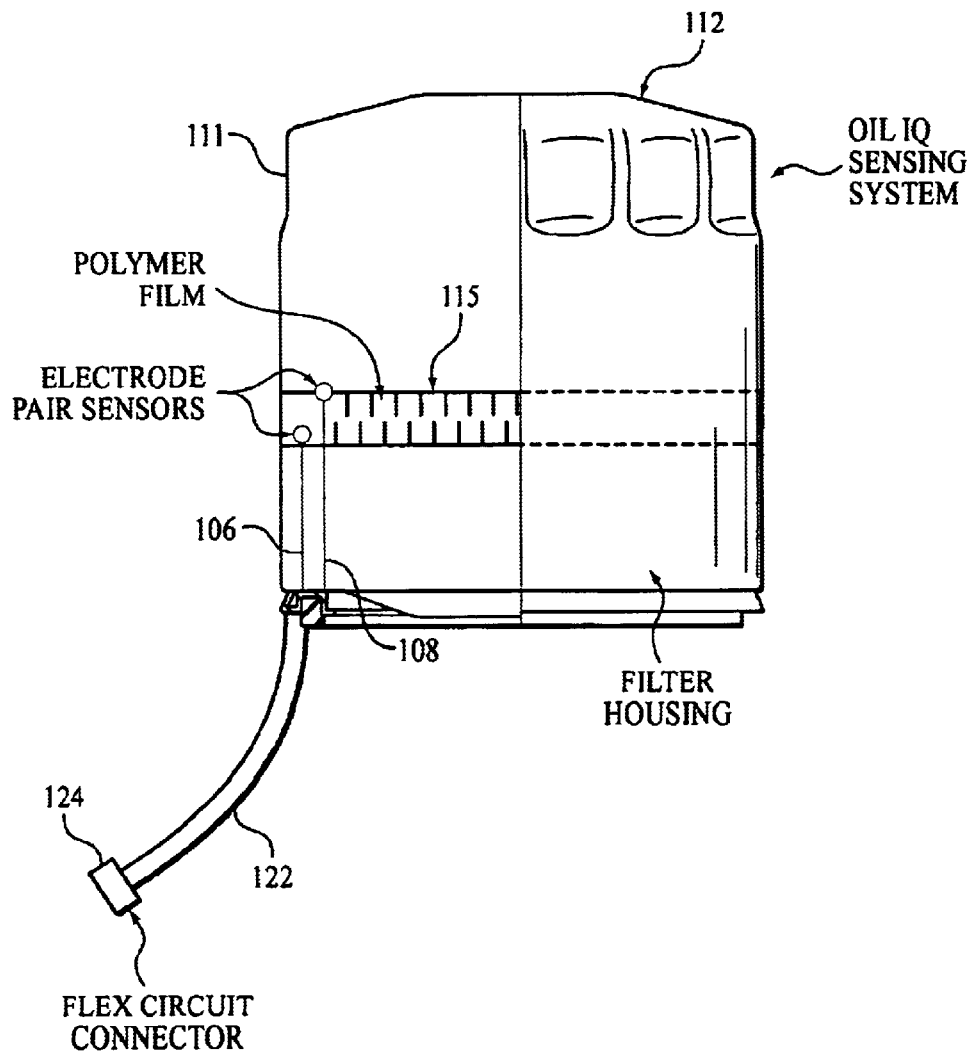
FIG. 2 is a side plan view of an oil filter, partially in cross-section, incorporating an oil quality sensor therein in accordance with a second embodiment of the invention.

FIG. 2 shows another oil filter 112 with a sensor 115 according to a second embodiment of the present invention mounted therein. In this second embodiment, the sensor 115 is provided as a cylindrical band attached to an inner wall of the oil filter housing 111. The system, in this second embodiment, also includes a flex cable 122 and a disconnectable plug 124, and suitable connecting wires 106, 108 are also provided, to electrically connect the interdigitated electrode pairs of the sensor 115 to the flex cable 122.

2. The Sensor

First Embodiment

Referring back to FIG. 1, it will be seen that the sensor 15 includes a plurality of spaced-apart electrode pairs, attached to a nonconductive polymeric substrate 34. A first electrode connector strip 36 extends laterally on the substrate 34, and has a plurality of spaced apart individual electrodes 37 extending transversely outwardly therefrom and in electrical communication therewith. Similarly, a second electrode connector strip 38 extends laterally on the substrate 34 parallel to the first connector strip 36, and the second connector strip has a plurality of spaced apart individual electrodes 39 extending transversely inwardly therefrom, and in electrical communication therewith. In this first embodiment, the respective sensor electrodes 37, 39 of the first and second connector strips 36, 38 may be interdigitated with one another, and are preferably arranged in a curved array, as shown.

The electrode pairs may be formed as a thin-film conductive coating applied over the substrate. Where used, this conductive coating may be applied to the substrate by stencil, screen-printing or ink-jet printing to provide a low-cost sensor. The material making up the connector strips 36, 38 and their respective electrodes 37, 39 is applied as a flowable conductive ink which can be applied by stencil, silk-screen, or inkjet printer. One commercially available conductive ink, which is suitable for use in the practice of the present invention, is sold by Methode Electronics, Inc. of Chicago, Ill. as product No. 1212.

The sensor 15 includes at least ten pairs of electrodes, more preferably at least 20 pairs of electrodes, and may include 25 electrode pairs.

For such a sensor array configuration, the equivalent electrical circuit is a set of several capacitors in parallel. Each electrode pair forms a capacitor element in the parallel circuit. The capacitance of each pair of electrodes may be added together to create an equivalent total capacitance for the sensor array.

Second Embodiment

Figure 3:
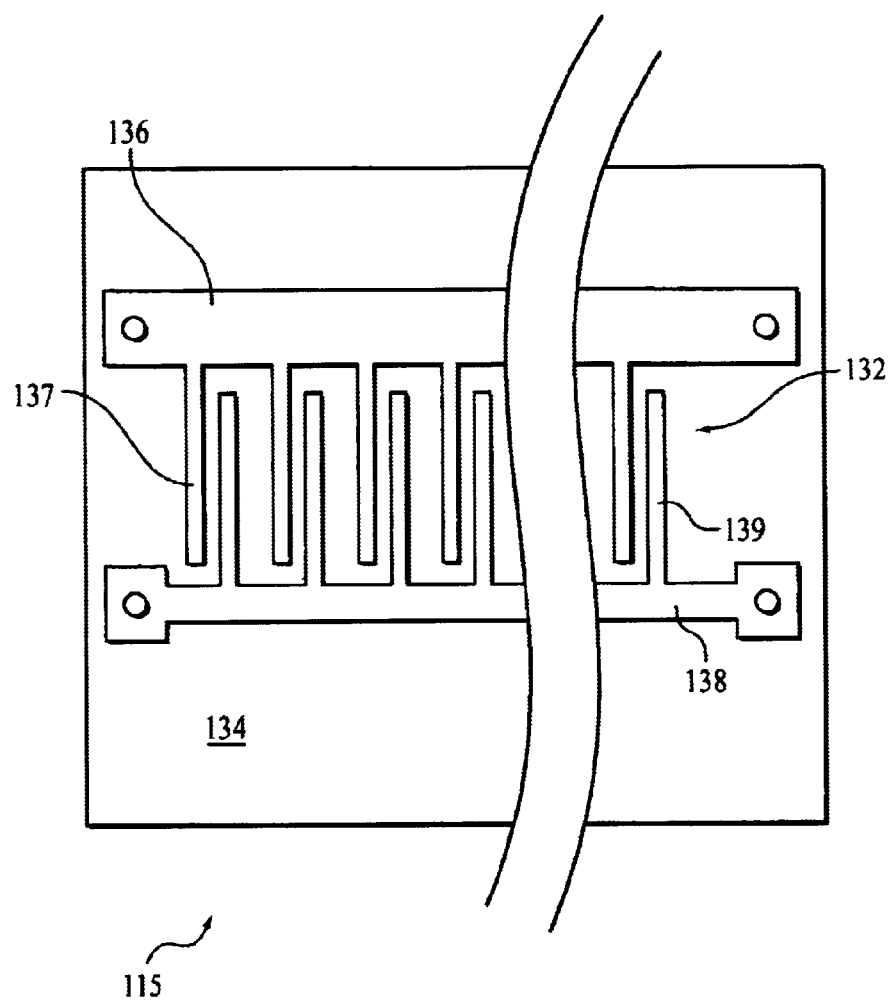
FIG. 3 is a plan view of a linear sensor array in accordance with the sensor of FIG. 2, partially broken away.

Referring now to FIG. 3, it will be seen that in the embodiment of FIG. 2, similar to the arrangement of parts in the first sensor 15, the sensor 115 in this second embodiment includes a plurality of spaced-apart electrode pairs 132, attached to a nonconductive polymeric substrate 134. A first electrode connector strip 136 extends laterally on the substrate 134, and has a plurality of spaced apart individual electrodes 137 extending transversely downwardly therefrom, and in electrical communication therewith. Similarly, a second electrode connector strip 138 extends laterally on the substrate 134 parallel to the first connector strip 136, and the second connector strip has a plurality of spaced apart individual electrodes 139 extending transversely upwardly therefrom, and in electrical communication therewith. The sensor electrodes of the first and second connector strips 136, 138 may be interdigitated with one another, and are preferably arranged in a linear array, as shown.

This multi-electrode design provides advantages over sensors using only a single pair of electrodes. Each electrode pair acts as an independent sensor element, and provides an "averaged" sensor signal output. This signal-averaging may potentially reduce operational electromagnetic interference (EMI) noise, which improves the signal-to-noise ratio of the system. This multi-electrode design will also provide some redundancy support, increasing system reliability. If one pair of electrodes fails or is partially inactivated, the signal-averaging and the presence of multiple other electrode pairs means that the system will still function.

The substrate 34, 134 is formed from a flexible nonconductive polymeric material. Preferably, the substrate comprises a fluoropolymer. One example of a suitable material for use as the substrate is a fluoropolymer film sold by the 3M company of Minneapolis, Minn., in a thickness of 5 mil.

The flexibility and thinness of the sensor 15, 115 allows it to be placed in locations where the previously known oil quality sensors would not fit. In particular, the sensor 15, 115 may be placed on an oil-contacting surface of an oil filter, without requiring significant structural modification thereof.

In a first embodiment of the invention, as shown in FIG. 1, the sensor 15 may take the form of a substantially flattened annular band attached to the oil filter's tapping plate 14, at a location where the sensor 15 will be immersed in oil.

In a second embodiment of the invention, as shown in FIG. 2, the sensor 115 may take the form of a linear array of said electrode pairs, on a strip 134 of flexible substrate, extending in a substantially cylindrical band around an inner wall of the oil filter 112.

3. Function of the Sensor

It has been well established that when a wave-form signal is sent to a pair of closely spaced apart electrodes immersed in a dielectric material, such as a lubricating oil, the electrodes tend to function as a capacitor, and to reflect a modified form of the supplied signal. (See, e.g., U.S. Pat. No. 5,274,335 to Wang and U.S. Pat. No. 5,929,754 to Park et al., the disclosures of which are incorporated by reference). This reflected signal is referred to herein as a wave echo.

In general, oil having a higher quality will give a better quality of wave echo. Conversely, oil which is breaking down or deteriorating will tend to give a more distorted wave echo.

Figure 4:
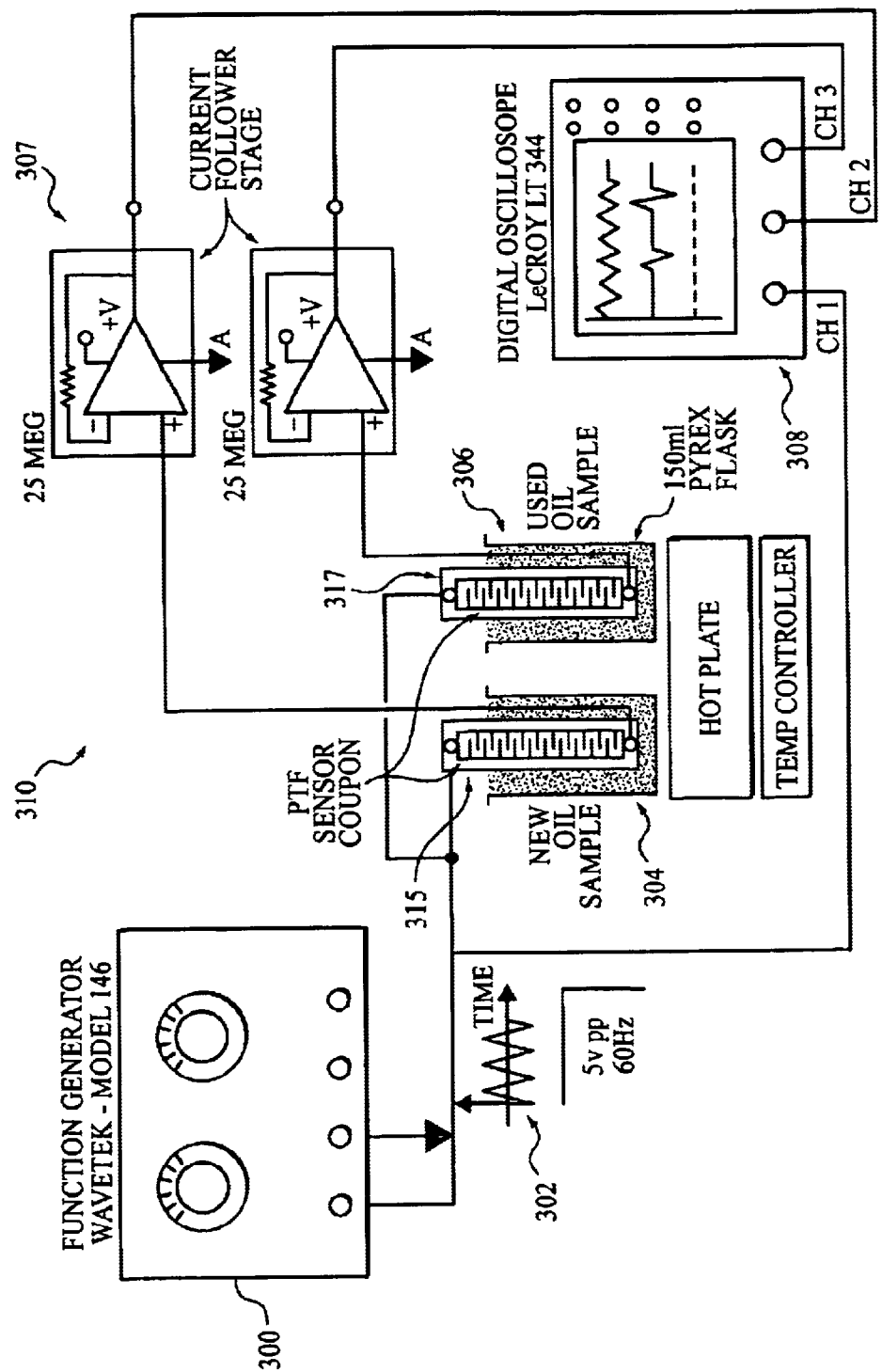
FIG. 4 is a simplified schematic diagram of a bench test of a sensor system according to the invention, comparing samples of new oil and used oil.

Referring now to FIG. 4, a bench test of a system 310 in accordance with the present invention is shown schematically.

Figure 5:
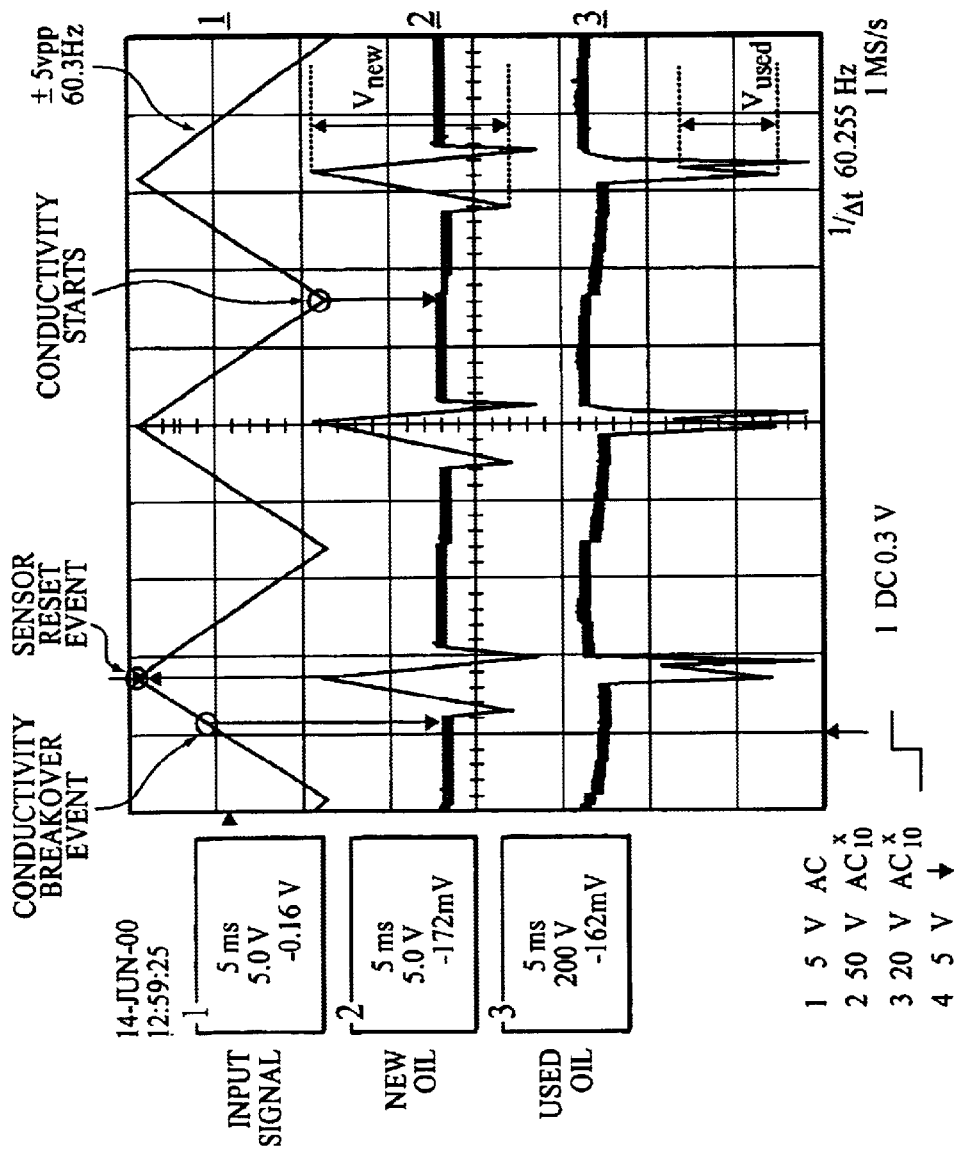
FIG. 5 is a two-dimensional printout of the results of the bench test of FIG. 4.

In the test system 310 of FIGS. 4–5, a wave generator 300 generates a forcing-function waveform 302 (i.e., triangular or reactive circuit resistor/capacitor time constant). The waveform 302 is applied to the sensor input electrodes of an identical set of sensors 315, 317, as a common voltage potential for all of the sensors' electrode pairs.

The sensors 315, 317 are placed in heated samples of engine oil. The first sensor 315 is immersed in a new, clean oil sample 304. The second sensor is immersed in a used oil sample 306, which has become deteriorated from extensive cycling through an engine.

A typical waveform frequency of 60 Hz is used. The maximum and minimum potentials of +6 volts and −6 volts are applied respectively. The output current from each electrode pair on the sensor array is summed together and sensed by the current follower amplifier. The current follower converts the sensor output current into an equivalent voltage (via a 25 mega-ohm resistor) for comparison with predetermined values.

The equivalent voltage is proportional to electrode surface area, peak applied voltage, and the number of electrode pairs. The equivalent voltage is inversely proportional to the distance between electrode pairs.

After the wave echo signal is reflected from the sensors, it is converted by a potentiostat circuit 307 to an equivalent voltage, and is forwarded to a digital oscilloscope 308 for a visual readout. This readout is shown in more detail in FIG. 5.

As seen from the readout in FIG. 5, initially, when the oil sample is clean and fresh, the wave echo is relatively clean and distinct, and resembles the original signal to a certain extent. As the oil sample becomes deteriorated, the wave echo becomes less defined and the voltage differential decreases significantly. In the system 10 as applied to a vehicle, once the equivalent voltage drops below a threshold value, a signal is sent from the control module 16 to activate a trouble code or a 'change oil' light 30 on the vehicle dashboard, to inform the driver that an oil change is needed.

4. Method

The present invention also relates to a method for detecting a condition of a motor oil, comprising a first step of attaching a sensor 15 to a removable oil filter 12, the sensor including a plurality of spaced apart electrode pairs mounted on a nonconductive film substrate 34.

The next step of the method involves immersing the sensor in oil. Most preferably, that is done by mounting the oil filter 12 on an automotive engine (not shown) and operating the engine.

The next steps of the method involve applying an electric current waveform to the sensor 12, measuring an electromagnetic wave reflected by the sensor 12; and comparing an equivalent value of the measured electromagnetic wave to a predetermined value. This comparison may be done by suitable electronics provided in the control module 16.

Although the present invention has been described herein with respect to a preferred embodiment thereof, the foregoing description is intended to be illustrative, and not restrictive. Those skilled in the art will realize that many modifications of the preferred embodiment could be made which would be operable. All such modifications which are within the scope of the claims are intended to be within the scope and spirit of the present invention.

What is claimed is:

1. An oil quality sensing system, comprising:

an oil filter;

a conductivity sensor attached to the oil filter, said conductivity sensor comprising a plurality of spaced apart electrode pairs mounted on a nonconductive film substrate, configured as a linear array or said electrode pairs extending in a band around an inner wall of the oil filter;

a waveform generator;

a measuring device for measuring a signal reflected by the sensor, a comparing device, and a signal generator.

2. An oil quality sensing system, comprising:

an oil filter;

a conductivity sensor attached to the oil filter, said conductivity sensor comprising a plurality of spaced apart electrode pairs mounted on a nonconductive film substrate, configured as a substantially circular array of said electrode pairs extending in an annular band around the underside of a tapping plate of said oil filter;

a waveform generator;

a measuring device for measuring a signal reflected by the sensor, a comparing device, and a signal generator.

3. An oil quality sensing system, comprising:

an oil filter;

a conductivity sensor attached to the oil filter, said conductivity sensor comprising a plurality of spaced apart electrode pairs mounted on a nonconductive film substrate;

a waveform generator;

a measuring device for measuring a signal reflected by the sensor, a comparing device, a signal generator; and a flexible electrical cable, electrically connected to said sensor and extending away from the oil filter, and a disconnectable plug attached to the cable.

4. A sensor for immersing placement in oil to monitor the condition thereof, said sensor comprising:

a nonconductive film of a polymeric substrate; and plurality of spaced apart electrode pairs applied to a first surface of the substrate; and a pressure-sensitive adhesive applied to a second surface of the substrate opposite the first surface.

5. A sensor for immersing placement in oil to monitor the condition thereof, said sensor comprising:

a nonconductive film of a polymeric substrate;

a plurality of spaced apart electrode pairs applied to a first surface of the substrate;

a first electrode connector strip extending laterally on the substrate;

a plurality of spaced apart electrodes extending from said first connector strip and in electrical communication therewith;

a second electrode connector strip extends laterally on the substrate, spaced from the second connector strip; and a plurality of spaced apart electrodes extending from said second connector strip and in electrical communication therewith.

6. The sensor of claim 5, wherein the electrodes of the first and second connector strips are interdigitated.

* * * * *